US006365406B1

(12) United States Patent
Phillips et al.

(10) Patent No.: US 6,365,406 B1
(45) Date of Patent: Apr. 2, 2002

(54) ENHANCERS OF NET PHOTOSYNTHESIS AND METHODS OF ENHANCING NET PHOTOSYNTHESIS

(75) Inventors: Donald A. Phillips; Cecillia M. Joseph, both of Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/193,801

(22) Filed: Nov. 17, 1998

(51) Int. Cl.$^7$ .............................................. A01N 63/00

(52) U.S. Cl. ..................... 435/420; 47/58.1; 504/116.1; 504/353

(58) Field of Search ........................... 47/58.1; 435/420

(56) References Cited

U.S. PATENT DOCUMENTS

| | | | |
|---|---|---|---|
| 4,704,161 A | | 11/1987 | White et al. |
| 4,789,436 A | | 12/1988 | Greenbaum |
| 5,403,583 A | | 4/1995 | Liu et al. |
| 5,415,672 A | | 5/1995 | Fahey et al. |
| 5,597,400 A | | 1/1997 | Nonomura et al. |
| 5,919,448 A | * | 7/1999 | Maekawa et al. |
| 5,935,571 A | * | 8/1999 | Aino et al. |

FOREIGN PATENT DOCUMENTS

| | | |
|---|---|---|
| JP | 60115501 | 6/1985 |
| JP | 01086822 | 3/1989 |
| JP | 03109304 | 5/1991 |
| JP | 04166017 | 6/1992 |
| WO | WO 96/21737 A1 | 7/1996 |
| WO | WO 97/01572 A1 | 1/1997 |

OTHER PUBLICATIONS

Strzelczyk, et al., "Synthesis of Auxins from Tryptophan and Tryptophan–precursors by Fungi Isolated from Mycorrhizae of Pine (*Pinus silvestris* L.)"; *ACTA Microbiologica Polonica*, vol. 26, No. 3, pp. 255–264 (1977).
Ryle, et al., "The Respiratory Costs of Nitrogen Fixation in Soyabean, Cowpea, and White Clover"; *Journal of Experimental Botany*, vol. 30, No. 114, pp. 145–153 (Feb, 1979).
DeJong, et al., "Nitrogen Stress and Apparent Photosynthesis in symbiotically Grown *Pisum sativum* L.", *Plant Physiol*. vol. 68, pp 309–313 (1981).
M.E. Brown, "Plant Growth Substances Produced by Micro-–organisms of Soil and Rhizosphere"; *J. appl. Bast.*, 35:443–451 (1972).
Volpin, et al., "Respiratory Elicitors from *Rhizobium meliloti* Affect Intact Alfalfa Roots"; *Plant Physiol.*, 116:777–783 (1998).
Keel, et al., "Pseudomonads as Antagonists of Plant Pathogens in the Rhizosphere: Role of the Antibiotic 2,4–Diacetylphloroglucinol in the Suppression of Black Root Rot of Tobacco"; *Symbiosis*, 9:327–341 (1990).

Raaijmakers, et al., "Natural Plant Protection by 2,4–Diacetylphloroglucinol–Producing Pseudomonas ssp. in Take–All Decline Soils"; *Molecular Plant–Microbe Interactions*, vol. 11, No. 2, pp. 144–152 (1998).
Zhang, et al., "Phosphoenolpyruvate Carboxylase Protein Kinase from Soybean Root Nodules: Partial Purification, Characterization, and Up/Down–Regulation by Photosynthate Supply from the Shoots"; *Archives of Biochemistry and Biophysics*, vol. 343, No. 2, pp. 260–268 (Jul. 1997).
J.J. Oertli, "Exogenous application of vitamins as regulators for growth and development of plants—a review";*Z. Pflanzenernahr. Bodenk.*, 150, 375–391 (1987).
Lugtenberg, et al., "Microbial stimulation of plant growth and protection from disease"; *Current Opinion in Biotechnology*, 2:457–464, (1991).
Barea, et al., "Impact on Arbuscular Mycorrhiza Formation of Pseudomonas Strains Used as Inoculants for Biocontrol of Soil–Borne Fungal Plant Pathogens"; *Applied and Environmental Microbiology*, vol 64, No. 6, pp. 2304–2307, (1998).
Naseby, et al., "Impact of wild–type and genetically modified *Pseudomonas fluorescens* on soil enzyme activities and microbial population structure in the rhizosphere of pea"; *Molecular Ecology*, 7:617–625 (1998).
Brimecombe, et al., "Effect of genetically modified *Pseudomonas fluorescens* strains on the uptake of nitrogen by pea from $^{15}$N enriched organic residues"; *Letters in Applied Microbiology* 26:155–160 (1998).
Fenton, et al., "Exploitation of Gene(s) Involved in 2,4–Diacetylphloroglucinol Biosynthesis to Confer a New Biocontrol Capability to a Pseudomonas Strain"; *Applied and Environmental Microbiology*, vol. 58, No. 12 pp. 3873–3878 (Dec. 1992).
Boadbent, et al., "C–Acetylphloroglucinols From *Pseudomonas fluorescens*"; *Phytochemistry*, vol. 15, pp. 1785 (1976).
Shanahan, et al., "Isolation, trace enrichment and liquid chromatographic analysis of diacetylphloroglucinol in culture and soil samples using UV and amperometric detection"; *Journal of Chromatography*, 606:171–177 (1992).
O.P. Jones, "Effect of phloridzin and phloroglucinol on apple shoots"; *Nature* vol. 262 pp. 592 (Jul. 1976).

(List continued on next page.)

Primary Examiner—Leon B. Lankford, Jr.
(74) Attorney, Agent, or Firm—Townsend and Townsend and Crew LLP

(57) ABSTRACT

The present invention provides novel enhancers of photosynthesis and methods of using same. In one embodiment, the enhancer is derived from a microorganism. In alternative embodiments, the compounds are microbial extracts, a microbial secretion products, and microbially generated natural products. The invention also provides a method for increasing net photosynthesis in a plant by applying an agent comprising triacetylphloroglucinol, diacetylphloroglucinol or monoacetylphloroglucinol to the plant in an amount effective in increasing net photosynthesis in the plant.

21 Claims, No Drawings

OTHER PUBLICATIONS

Grochowska, "Chromatographic Degradation of Phloridzin"; *Plant Physiol.* 41:432–436, (1966).

Marré, et al., "Azione Di Stimolo Della Florizina Sulla Fotosintesi E Sulla Fotolisi Da Parte Di Cloroplasti Isolati"; *Nuovo Giornale Botanico Italiano*, vol. LXII, p. 566, (1955).

Shanahan, et al., "Liquid chromatographic assay of microbially derived phloroglucinol antibiotics for establishing the biosynthetic route to production, and the factors affecting their regulation"; *Analytica Chimica Acta*, 272:271–277 (1993).

* cited by examiner

ENHANCERS OF NET PHOTOSYNTHESIS AND METHODS OF ENHANCING NET PHOTOSYNTHESIS

STATEMENT AS TO RIGHTS TO INVENTIONS MADE UNDER FEDERALLY SPONSORED RESEARCH AND DEVELOPMENT

This invention was made with Government support under Grant No. IBN-9722988, awarded by the National Science Foundation. The Government may have certain rights in this invention.

INTRODUCTION

The present invention provides a novel enhancers of net photosynthesis and methods of enhancing net photosynthesis in plants. Due to the ever increasing need to grow crops more efficiently, the ability to increase a plant's growth rate would be of great social and economic value. An attractive biochemical target to accomplish this is the plant's ability to fix carbon dioxide by photosynthesis. The ability to enhance net photosynthesis will allow the grower to generate a plant that is faster growing and/or has increased biomass in, for example, storage products, such as starch (polysaccharides), protein or fats.

Researchers have been investigating means to boost a plant's photosynthetic rate in a variety of ways. Some examples include exposing a plant to light with the same wavelengths as sunlight (see, e.g., JP04166017); generating transgenic plants with exogenous genes involved in photosynthesis (see, e.g., WO 96/21737); application of various chemicals to increase the rate of photosynthesis (see, e.g., JP03109304, U.S. Pat. Nos. 4,704,161; 5,597,400); and, applying chemicals to suppress photorespiration, resulting in an increase in the efficiency of photosynthesis (see, e.g., JP01086822, JP60115501, JP55136205, JP55036437).

However, prior to this invention, no enhancers of net photosynthesis have been identified. Furthermore, the present invention taps a rich, yet to date, uptapped source, of enhancers of net photosynthesis from microorganisms, particularly, bacteria. Identification of enhancers of net photosynthesis from microorganisms would offer many benefits. For example, the reagent, as a natural product, can be generated on a large, industrial scale using conventional techniques. This eliminates the need to structurally analyze and/or synthetically produce the bioactive component of the microbial extract. Furthermore, if the microorganism can grow in soil or can colonize plant roots, application of the microbe to the soil could be equivalent to applying the bacterial natural product or extract itself. If the genetic mechanism responsible for producing the bioactive agent is found, transgenic microorganisms can be constructed. Thus, any soil-borne or plant (e.g., root, leaf)-colonizing microorganism can be recombinantly manipulated to generate an enhancer of net photosynthesis of the invention.

The present invention, by providing novel enhancers of net photosynthesis, particularly enhancers that can be synthesized by microbes and isolated from microbial extracts, fulfills these, and other, needs.

SUMMARY OF THE INVENTION

The present invention provides novel enhancers of net photosynthesis and methods of using same. In alternative embodiments, the enhancer is a microorganism, or, is an isolated or purified composition derived from a microorganism. In alternative embodiments, the compounds are microbial extracts, a microbial secretion products, and microbially generated natural products.

The invention also provides methods for increasing net photosynthesis in a plant by applying an agent comprising triacetylphloroglucinol, diacetylphloroglucinol or monoacetylphloroglucinol to the plant in an amount effective in increasing net photosynthesis in the plant. The triacetylphloroglucinol, diacetylphloroglucinol (DAPG) or monoacetylphloroglucinol can be natural products derived from, or purified from (e.g., a bacterial extract) a microorganism, or they can be generated by organic synthesis (in fact, DAPG can be purchased from commercial sources). In a preferred embodiment, the agent thus applied is 2,4,-diacetylphloroglucinol.

In various embodiments, the enhancer of net photosynthesis can be applied to any part of the plant, including, e.g., the root of the plant.

In the methods of the invention, the net photosynthesis-enhancing agent thus applied can comprise a bacterium, which can be, e.g., in preferred embodiments, Sinorhizobium meliloti, or Pseudomonas fluorescens. The bacterium can be applied in a concentration of about $10^7$ to about $10^8$ bacteria per mL. Alternatively, the agent can comprise a bacteria culture media or an isolated bacterial product. Bacterial products can be isolated by any means, including, e.g., various chromatographic techniques, such as HPLC.

While the net photosynthesis-enhancing agents of the invention can be applied in any concentration (or estimated concentration or level of purity, if the agent is an extract from a microorganisms), in alternative embodiments, the agent is applied in a concentration of about 1 nM to about 1.0 M, from about 10 nM to about 100 mM, and 50 nM to about 100 nM to the root of said plant. As discussed below, the amount of exact amount of agent necessary to increase net photosynthesis in a given situation under a specific set of conditions can be determined by the skilled artisan using routine testing, as described herein.

In the methods of the invention, the photosynthesis-enhancing agent can be applied to the plant in multiple applications, for example, every 24 to 48 hours.

The invention provides methods for increasing net photosynthesis in any plant; in various embodiments, the plants can be angiosperms, which can be monocotyledonous plants or dicotyledonous plants. The dicotyledonous plant can be a legume, which can be an alfalfa plant.

The invention further provides a method for increasing net photosynthesis in a plant by applying an agent comprising a bacterium, wherein the bacterium is applied in an amount effective to increase net photosynthesis in the plant, wherein the bacterium is selected from the group consisting of Sinorhizobium meliloti and Pseudomonas fluorescens.

Also provided is a method for increasing net photosynthesis in a plant comprising applying to the plant an agent comprising an isolated bacterial product, wherein the agent is applied in an amount effective to increase net photosynthesis in the plant, wherein the bacterium is selected from the group consisting of Sinorhizobium meliloti and Pseudomonas fluorescens. The isolated bacterial product thus applied can comprise a Sinorhizobium meliloti bacterial product whose UV visible absorbance analysis contains maxima at about 216 nm, about 260 nm, about 351 nm, and about 390 nm in methanol/water.

In alternative embodiments of the methods, the isolated bacterial product thus applied can comprise a Sinorhizobium meliloti bacterial product whose UV visible absorbance analysis contains maxima at about 222 nm, about 266 nm, about 370 nm, and about 445 nm in methanol/water; or whose proton nuclear magnetic resonance (NMR) analysis contains signals consistent with the presence of two separate and distinct protons at about 7.75 to about 8.1 ppm for every two aromatic methyl groups, wherein the presence of the two proton signals around 8.0 indicate the protons are part of a heterocylic structure. The NMR analysis can further contain an additional proton signal between about 8 ppm and about 9 ppm, which is consistent with a proton on an aromatic N atom; or, can further contain signals consistent with the presence of several aromatic moieties linked together. In another embodiment of the methods, the *Sinorhizobium meliloti* bacterial product can have a molecular weight (MW) of about 770 amu as estimated by unit resolution mass spectrometry analysis; or, a MW of about 752 amu as estimated by unit resolution mass spectrometry analysis.

The invention also provides isolated bacterial products for increasing net photosynthesis in a plant. The bacterial products can be derived from *Sinorhizobium meliloti* and have a UV visible absorbance analysis containing maxima at about 216 nm, about 260 nm, about 351 nm, and about 390 nm in methanol/water; or, the product can have a UV visible absorbance analysis containing maxima at about 222 nm, about 266 nm, about 370 nm, and about 445 nm in methanol/ water. In one embodiment, the *Sinorhizobium meliloti* bacterial product can have a proton NMR analysis containing signals consistent with the presence of two separate and distinct aromatic protons at about 7.75 to about 8.1 ppm for every two aromatic methyl groups, wherein the presence of the two proton signals around 8.0 indicates the protons are part of a heterocylic structure. The proton NMR analysis can further contain an additional proton signal at approximately 8.5 ppm, which is consistent with a proton on an aromatic N atom. The composition's proton NMR analysis can further contain signals consistent with the presence of several aromatic moieties linked together. The isolated *Sinorhizobium meliloti* bacterial product can also have a MW of about 770 amu as estimated by unit resolution mass spectrometry analysis; or, it can have MW of about 752 amu as estimated by unit resolution mass spectrometry analysis.

A further understanding of the nature and advantages of the present invention may be realized by reference to the remaining portions of the specification, the figures and claims.

All publications, GenBank Accession references (sequences), ATCC Deposits, patents and patent applications cited herein are hereby expressly incorporated by reference for all purposes.

DETAILED DESCRIPTION OF THE INVENTION

This invention is a first description of novel, bacterially derived, enhancers of net photosynthesis. Use of enhancers of net photosynthesis from microbial sources confers many advantages, especially in the production of the reagents and their application to plants and crops. As natural products, the photosynthetic enhancers can be produced on a large, economical scale using conventional industrial techniques.

The invention provides various concentrations and levels of purity of these novel enhancers of net photosynthesis. For example, the bacteria known to produce the enhancers of the invention can be directly applied to a plant. Alternatively, the enhancer can be isolated (term defined below) before applying to the plant. As used herein, such isolation includes substantially pure enhancing reagents, relatively crude preparations, and any variation thereof, as long as the preparation has the ability to enhance photosynthesis. If the enhancer is secreted into a microbial culture medium, the medium itself can be applied, or, it may only be necessary to concentrate the medium. Thus, significant quantities of active reagent can be produced and used without the need for substantial purification or structural characterization of the active chemical entity in the identified natural product.

The level of purity or concentration of an enhancer of net photosynthesis of the invention needed for a particular situation may vary depending on, e.g., what plants are being treated, where and how the plants are treated (e.g., spraying on leaves, liquid application to soil, hydroponic cultures (e.g., Wang (1996) *Biol. Trace Elem. Res.* 55:147–62; Ling (1993) *J Chromatogr.* 643:351–5), "aeroponic" growth on moistened filter paper in Petri dishes (e.g., Tari (1990) *Acta Biol Hung* 41:387–97) growth in nutrient solution-circulating growth chambers (e.g., Shima (1997) *Mutat Res* 1997 Dec 12;395(2–3): 199–208), injections into the plant) and the like, which can be determined by the skilled artisan with routine screening and testing.

Being bacterial natural products, significant quantities of an enhancer of the invention can be identified, produced and used without the need for purification to homogeneity or structural characterization. Furthermore, if the microorganism producing an enhancer of the invention can grow in soil or can colonize the plant (e.g., roots, leaves), application of the microbe to the soil would be sufficient to enhance net photosynthesis.

Alternatively, if the active reagent is purified and/ structurally identified, biosynthetic and genetic mechanisms responsible for producing the bioactive agent by the microbe can also be found. Using this information, transgenic microorganisms capable of synthesizing the enhancers of the invention can then be constructed. Thus, any soil-borne or plant (e.g., root, leaf)-colonizing microorganism can be recombinantly manipulated to generate an enhancer of net photosynthesis of the invention.

In an alternative embodiment, the invention provides a novel method for increasing net photosynthesis in a plant by applying an agent containing triacetylphloroglucinol, diacetylphloroglucinol, or monoacetylphloroglucinol to the plant in an amount effective for increasing net photosynthesis in the plant. These enhancers of net photosynthesis can also be synthesized as natural products by bacterial and used with the advantages described above.

However, it is not necessary that the enhancers of the invention be natural products of microbes. In one embodiment, the enhancers of net photosynthesis are organically synthesized, as described below.

DEFINITIONS

To facilitate understanding the invention, a number of terms are defined below.

As used herein, the terms "isolated" or "isolate," when referring to a molecule or compound, such as, e.g., an extract or isolate from a microorganism, such as a bacterium, means that the molecule or composition is separated from at least one other compound, such as a protein, a sugar, a lipid, a nucleic acid (e.g., RNA, DNA), or other contaminants with which it is associated in vivo or in its naturally occurring state. Thus, an enhancer of net photosynthesis of the invention is considered isolated when it has been separated from at least one other component with which it is associated in vivo or in vitro, e.g., cell membrane, as in a cell extract, or from a culture media into which the compound had been secreted by a microbe. For example, enhancers of net photosynthesis as bacterial products are isolated to varying degrees of purity using column chromatography and high performance liquid chromatography (HPLC), as described below. Furthermore, an isolated enhancer of the invention can also be substantially pure. An isolated composition can be in a homogeneous state and can be in a dry or an aqueous solution. Purity and homogeneity can be determined, e.g., using analytical chemistry techniques such as polyacrylamide gel electrophoresis (SDS-PAGE) or HPLC.

As used herein, the terms "bacterium" and "bacteria" incorporate their common usage, and includes, e.g., all genera and species from the Prokaryotae (Monera) Kingdom (e.g., bacteria, including Eubacteria and Archeabacteria), as described in further detail below. The methods of the invention include application of any microorganism that can generate a net photosynthesis-enhancing agent of the invention, including, e.g., *Sinorhizobium meliloti* (also known as *Rhizobium meliloti*), and *Pseudomonas fluorescens* (see Examples, below). As used herein, the term "bacterial product" incorporates its common usage, and includes, e.g., any and all compositions associated with (e.g., generated or synthesized by) a bacteria, internal or external or secreted, including the entire bacterium.

As used herein, the terms "monoacetylphloroglucinol," "diacetylphloroglucinol," and "triacetylphloroglucinol," incorporate their broadest chemical meaning. Diacetylphloroglucinol has the chemical formula $C_{10}H_{10}O_5$. One form of diacetylphloroglucinol is 2,4-diacetylphloroglucinol, also known as 2,4-diacetyl-1,3,5-benzenetriol.

As used herein, the term "increase in net photosynthesis" means that, over a time period, more photosynthesis than respiration (including the sum of photorespiration and dark respiration) occurs in the plant as a whole. A variety of means are available to the skilled artisan for evaluating and measuring a net increase in photosynthesis in a plant in practicing the methods of the invention. For example, if there is an increase in net photosynthesis, then the increase in the amount of oxygen gas released from the plant is greater than the increase in the amount of carbon dioxide gas released (which is, as discussed below, detectable and quantifiable). Furthermore, if there is an increase in net photosynthesis, the plant normally increases its biomass, which can be determined by, e.g., measuring an accumulation of photosynthates or an increase in plant "dry weight." However, the increase in biomass generated by the net increase in the photosynthetic reaction may not be uniform throughout the plant or may be transient. For example, when increased amounts of photosynthate (generated by net increase in photosynthesis) are transported to the roots and used to drive an increase rate of dark respiration in the root, the photosynthates are consumed in the dark respiration reaction; they are not used to increase the dry weight (biomass) of the root. Thus, the term "enhancer of net photosynthesis" indicates that a composition, an extract, a microorganism, can increase net photosynthesis in a plant, as can be determined by methods described herein. The compositions of the invention can be identified and evaluated by determining their ability to increase net photosynthesis in a plant using these routine tests.

As used herein, the term "plant" includes whole plants, plant organs (e.g., leaves, stems, flowers, roots, etc.), plant protoplasts, seeds and plant cells and progeny of same. The class of plants which can be used in the method of the invention includes angiosperms (monocotyledonous and dicotyledonous plants), as well as gymnosperms. It includes plants of a variety of ploidy levels, including polyploid, diploid, haploid and hemizygous (see discussion, infra).

Determining Net Photosynthesis in a Plant

The invention provides novel methods and compositions for increasing net photosynthesis in a plant. These methods comprise applying to the plant agents that include triacetylphloroglucinol, diacetylphloroglucinol and monoacetylphloroglucinol, and novel isolated bacterial products of the invention, as described herein. These agents are applied to the plant in amounts effective for increasing net photosynthesis in the plant.

To evaluate the levels of purity of an agent or bacterial isolate, the effective amounts of agent needed for particular application, the sites and modes of delivery, the frequency of applications needed, and the like, any means of measuring rates and levels of net photosynthesis can be used. Such routine testing means are well known in the art and include, e.g., increases in, e.g., dry weight; carbon dioxide uptake, oxygen generation, carbon assimilation, plant storage products, such as, e.g., polysaccharides (e.g., starches), lipids, proteins and the like (depending on the plant type or stage in life cycle).

In practicing the methods of the invention, enhancement of net photosynthesis can also be evaluated by analysis of various steps in the photosynthetic biochemical mechanism. For example, the oxidation (redox) state of photosynthetic metalloproteins can be determined by, e.g., UV absorbance changes.

Measuring Net Increase in Carbon Dioxide Uptake by a Plant

An agent or bacterial isolate of the invention can be evaluated by determining the level of net increase in carbon dioxide ($CO_2$) gas uptake by the plant over a measured time period. Any means can be used to measure a net increase in carbon dioxide uptake by the plant, such as by gas chromatograph, as described in detail below. See also, e.g., Borjesson (1992) *Appl. Environ. Microbiol.* 58:2599–2605.

Measuring Net Increase in Oxygen Generated by a Plant

An agent or bacterial isolate of the invention can be evaluated by determining the level of net increase in oxygen gas ($O_2$) generated by the plant over a measured time period. Any means can be used to measure a net increase in oxygen generated by the plant, such as by gas chromatograph, as described in detail below (see Example 1, below). See also, e.g., use of the "Barcroft manometer" (Umbreit, W. W., R. H. Burris, J. F. Stauffer. 1972. Manometric & Biochemical Techniques, p. 111–125); and, Greenbaum, U.S. Pat. No. 4,789,436, describing methods and apparatus for nondestructive in vivo measurement of photosynthesis in plants using oxygen electrodes.

Measuring Net Increase in Radioactive Carbon Uptake by a Plant

An agent or bacterial isolate of the invention can be evaluated by determining the level of net increase in carbon assimilation by the plant over a measured time period. Any means can be used to measure a net increase in carbon assimilation by the plant. In a preferred embodiment, a net increase in carbon assimilation is measured by a net increase in radioactive carbon (radioisotope $^{14}C$) uptake by a plant, as described, e.g., in the isotopic assay for measuring net photosynthesis with $^{14}CO_2$ in Sheikholeslam (1980) *Botanical Gazette* 141:48–52 (see Example 1, below). See also, e.g., Andralojc (1994) *Biochem J* 304:781–6.

Measuring Net Increase in Plant Photosynthates

Another preferred means to determine of there is a net increase in carbon assimilation of the plant over the measured time period is to measure a net increase in plant photosynthate levels. As defined above, plant photosynthates include, e.g., polysaccharides (e.g., starch, carbohydrates), oligosaccharides and monosaccharides. Any means can be used to measure an increase in the different classes and levels of photosynthates. See, e.g., Zhang (1997) *Arch Biochem Biophys* 343:260–8; Zhang (1997) *FEBS Lett* 410:126–30.

Measuring Net Increase in Dry Weight of a Plant

An agent or bacterial isolate of the invention can be evaluated by determining the level of net increase in dry weight by the plant over a measured time period. Any means can be used to measure a net increase in dry weight of the plant, see, e.g., Almazan (1997) *Plant Foods Hum Nutr* 50:259–68.

Any individual part of the plant (e.g., roots, leaves, stems, flowers, fruits) can be individually analyzed for which various individual constituents accumulate after a net increase in photosynthesis. For example, dry matter, protein, fat, ash, minerals (Ca, Fe, K, Mg, Na, Zn), vitamins (carotene, ascorbic acid, thiamin), and various other chemicals (e.g., acids) can be measured. This data will provide additional information to aid in the use of the enhancers of net photosynthesis of the invention by determining which bioconversion processes are mobilized by the reagent for biomass conversion into food or forms suitable for crop production. See, e.g., Almazan (1997) supra; Hung (1997) *Chemosphere* 35:959–77.

Measuring Photosynthesis

Photosynthesis can be monitored concurrently with any of the above means to measure an increase in net photosynthesis in the plant. Photosynthesis can be measured both before, during and after application of the agent or bacterial isolate of the invention to the plant. Any means known in the art can be used. For example, photosynthesis can be evaluated by measuring the redox state of a photosystem membrane (see, e.g., Stirbet (1998) *Theor. Biol.* 193(1): 131–51). Means to measure the redox state of a photosystem membrane of a plant are well known, e.g., using electron paramagnetic resonance (EPR) and flash photolysis (see, e.g., Hoshida (1997) *Biochemistry.* 36:12053–61; Gourovskaya (1997) *FEBS Lett* 414:193–6; Yruela (1996) *Biochemistry* 35:9469–74.

Selecting and Using Microorganisms

The methods of the invention include applying to a plant any microbe, e.g., any bacterium, capable of generating an enhancer of net photosynthesis of the invention. The bacterium, as defined above, can be, e.g., any member of the Prokaryotae (Monera) kingdom. While, without limitation, any bacteria can be used, preferred embodiments use and application of *Sinorhizobium meliloti, Pseudomonas fluorescens,* and species within the genera Rhizobium or Bradyrhizobium.

The agents and bacterial isolates of the invention can be applied as preparations purified to varying degrees, as extracts, or as secretion products of a microorganism. In one embodiment, a microorganism (which can generate a net photosynthesis-enhancing agent of the invention, either as a natural product, or because it has been recombinantly manipulated to secrete the agent) can be applied directly to the plant, e.g., the root, shoot, stem, leaf. In one embodiment, the agent or bacterial isolate, whether a microorganism, a composition derived from the microorganism, or a synthetic version of the agent, is applied to the soil or directly around or into the root of the plant.

Soil Dwelling or Root Colonizing Microorganisms

In a preferred embodiment, microorganisms that generate a net photosynthesis-enhancing agent of the invention which can live in soil or can colonize roots (e.g., in root rhizospheres) are used. For example, all microorganisms which are known to colonize roots are preferred embodiments to be used in the methods of the invention. The skilled artisan can further isolate root-colonizing microbes by, e.g., isolating root nodules and rhizospheres and determining rhizobial root microorganism populations (see, e.g., Petersen (1996) *FEMS Microbiol Lett* 142:271–276; Simons (1996) *Mol. Plant Microbe Interact.* 9:600–607). See also, Kloepper, et. al., U.S. Pat. Nos. 5,503,651, and 5,503,652, describing means to isolate bacterial strains from the rhizosphere.

Exemplary bacterial species, include, e.g., *Rhizobium meliloti,* which invade alfalfa root nodules to establish an effective nitrogen-fixing symbiosis (see, e.g., Cheng (1998) *J Bacteriol.* 180:5183–5191). *Pseudomonas fluorescens* are known to colonize the root tips of, e.g., alfalfa, tomato, radish, and wheat (see, e.g., Dekkers (1998) *Mol. Plant Microbe Interact.* 11:763–771. *Agrobacterium tumefaciens* is known to infect a variety of plant roots and other cell types (see, e.g., Matthysse (1998) *Appl. Environ. Microbiol.* 64:2341–2345). *Azospirillum brasilense* and *Pseudomonas aureofaciens* are known to infect the roots (rhizospheres) of, e.g., wheat (see, e.g., Pereg-Gerk (1998) *Mol. Plant Microbe Interact.* 11:177–187; Wood (1997) *J. Bacteriol.* 179:7663–7670).

Exemplary fungal root-colonizing species include, e.g., arbuscular mycorrhizal fungi, such as *Glomus mosseae, G. intraradices, Gigaspora rosea, Scutellospora castanea* (see, e.g., Burleigh (1998) *Gene* 216:47–53; van Tuinen (1998) *Mol. Ecol.* 7:879–887).

Preparing Net Photosynthesis-Enhancing Agents

Microorganisms that Generate Net Photosynthesis-Enhancing Agents

In one embodiment, the methods of the invention involve applying a microorganism that generates a net photosynthesis-enhancing agent of the invention, or a secretion product of that microorganism. Methodologies for culturing microorganisms, particularly in a large scale, are well known in the art, see, e.g., Moir (1990) *Bioprocess Technol* 9:67–94; Gailliot (1990) *Biotechnol Prog* 6:370–5.

Bacterial Extracts As Net Photosynthesis-Enhancing Agents

In various embodiments, the net photosynthesis-enhancing agents and bacterial extracts are isolated and purified from a microorganism or a microbial secretion. The isolation of the net photosynthesis enhancing agent or bacterial isolate can be accomplished using any methodology; for general information relating to standard purification procedures, including. e.g., selective precipitation with such substances as ammonium sulfate; electrophoresis, immunopurification, chromatography (such as HPLC, see Examples, below), and others, see, e.g., Scopes, *PROTEIN PURIFICATION: PRINCIPLES AND PRACTICE*, Springer-Verlag: New York (1982); VanBogelen (1995) *Biotechnol Annu Rev* 1:69–103; Evans (1995) *Biotechnology* 13:46–52; Perkins (1991) *J Chromatogr* 540:239–56; Sambrook, *MOLECULAR CLONING: A LABORATORY MANUAL* (2ND ED.), Vols. 1–3, Cold Spring Harbor Laboratory, (1989); *CURRENT PROTOCOLS IN MOLECULAR BIOLOGY,* Ausubel, ed. Greene Publishing and Wiley-Interscience, New York (1987). See also, e.g., Afeyan, et. al., U.S. Pat. No. 5,833,861, describing chromatography methods and matrix geometry's which permit high resolution, high productivity separation of mixtures of solutes, particularly biological materials.

For example, as described below in the Examples, a net photosynthesis enhancing agent or bacterial isolate of the invention can be in the form of crude extracts of bacterial cultures. In the Examples, microbial extracts are isolated from cultured *Sinorhizobium meliloti* as fractions using column chromatography and HPLC. The fractions are subsequently demonstrated to increase net photosynthesis in an alfalfa model plant system. Fractions which were able to increase net photosynthesis, as measured increased radioactive carbon-14 in the plant, were further analyzed by as variety of techniques, including mass spectrometry, proton nuclear magnetic resonance, and UV-visible absorbance analysis.

Acetylphloroglucinols As Net Photosynthesis-Enhancing Agents

The methods of the invention also use agents comprising triacetylphloroglucinol, diacetylphloroglucinol and monoacetylphloroglucinol in amounts effective for increasing net photosynthesis in a plant. These compounds were initially identified because they have general structural identity to the bacterial extract compounds D and Y of the invention (see below). Analysis of diacetylphloroglucinol (as described above for compounds D and Y, below), found that it increases net photosynthesis in plants by as much as 50% when it is applied to roots in nanomolar concentrations.

The triacetylphloroglucinol, diacetylphloroglucinol (DAPG) and monoacetylphloroglucinol agents of the invention can be generated synthetically (i.e., in vitro organic synthesis), or, can be isolated from any one of a number of bacterial which generate (and, in many cases, secrete) these compounds as natural products. For example, a number of soil bacteria, including, e.g., Pseudomonas species, produce diacetylphloroglucinol. See, e.g., Shanahan (1992) *J. of Chromatography* 606:171–177, describing purification of 2,4-diacetylphloroglucinol from *Pseudomonas fluorescens* by HPLC. See also, e.g., Shanahan (1993) *Analytica Chimica Acta* 272:271–277, describing a preparative chromatographic isolation method involving thin-layer and liquid chromatography to isolate monoacetylphloroglucinol and DAPG from bacteria. For description of the synthesis of triacetylphloroglucinol, see, e.g., Gulati (1943) *Org. Synth. Coll.* Vol II, page 522; Broadbent (1976) *Phytochemistry* 15:1785. For the synthetic generation of the triacetylphloroglucinol, DAPG and monoacetylphloroglucinol agents of the invention; see also, e.g., Campbell (1951) *J Am. Chem. Soc.* 73:2708–2712; Cronin (1997) *FEMS Microbiol. Ecology* 23:95–106. See, e.g., Yamaki (1994) *Phytotherapy Res.* 8:112–114, for a description of several phloroglucinols isolated from Chinese herbal drugs; and, Arisawa (1990) *Chem. Pharm. Bull.* 38:1624–1626; Bowden (1965) *J Pharm. Pharmacol.* 17:239–242; Hisada (1972) *Yakugaku Zasshi* 92:1124–1128.

Alternatively, bacteria or other microorganisms can be recombinantly manipulated to generate (or generate more) triacetylphloroglucinol, diacetylphloroglucinol and monoacetylphloroglucinol (or any of the other net photosynthesis-enhancing agents of the invention, as described herein). For example, see, e.g., Thomashow, et al., WO 97/01572, describing DNA sequences which function specifically in the synthesis of 2,4-diacetylphloroglucinol, and bacterial strains recombinantly manipulated to secrete this compound. See also, e.g., Barea (1998) *Applied and Environmental Microbiol.* 64:2304–2307; describing an genetically engineered Pseudomonas strain which is an overproducer of diacetylphloroglucinol; and, Naseby (1998) *Molecular Ecology* 7:617–625; Brimecombe (1998) *Letters in Applied Microbiol.* 26:155–160; Fenton (1992) *Applied and Environmental Microbiol.* 58:3873–3878.

Applying and Enhancer of Net Photosynthesis to a Plant

Selection of Plants

The methods of the invention and the net photosynthesis enhancing agents or bacterial isolates of the invention can be used to enhance net photosynthesis in essentially any plant. Thus, the invention incorporates use of (application to) a broad range of plants, including, e.g., species from the genera Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Phaseolus, Pisum, Pyrus, Prunus, Raphanus, Secale, Senecio, Sinapis, Solanum, Sorghum, Trigonella, Triticum, Vitis, Vigna, and, Zea, to name just a few.

Application Methodologies

The invention involves applying a net photosynthesis enhancing agent or a bacterial isolate to any part of a plant, including, e.g., roots, stems, leaves, seeds and shoots. For example, if the compound is to be applied to the root, it can be in a liquid applied to soil. Alternatively, it can be applied as organism per se, such as a soil-dwelling or root-colonizing microbe, and subsequently generated and secreted by to microorganism.

Alternatively, the net photosynthesis enhancing agent or bacterial isolate can be sprayed on leaves, injected into a stalk, and the like. See also, e.g., Lloyd, et. al., U.S. Pat. No. 5,739,081, describing water dispersible granules suitable for agricultural application, where biologically active substances are loaded into preformed absorbent granules. Luthra, et. al., U.S. Pat. No. 5,652,196, describes means to apply water soluble agents to plants in a variable, controlled release manner. Behel, Jr., et. al., U.S. Pat. No. 5,632,799, describes a dried particulate, hydrophilic gel as micronutrient delivery system to plants in soil. Aoki, et. al., U.S. Pat. No. 5,676,726, describes a matrix for application as a plant culture medium which can be used as a microorganism-immobilizing support capable of delivering a large population of microorganisms with long-term viability and improved colonization and growth rates, to plants in soil.

The net photosynthesis enhancing agent or bacterial isolate of the invention can also be applied to, e.g., seedlings or germinations incubated under hydroponic systems (see, e.g., Wang (1996) *Biol Trace Elem Res* 55:147–62.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are provided to illustrate the present invention, and not by way of limitation.

Example 1

Identifying Novel Microbial Enhancers of Net Photosynthesis by Measuring "Delayed" increases in Root Respiration The following example details methods for identifying novel bacteria and bacterial extracts that are net enhancers of photosynthesis by measuring their ability to increase "delayed" net root respiration in a plant. "Delayed" increases in root respiration are typically associated with an increase in net photosynthesis. A microorganism, a bacterial isolate, or a synthetic preparation thereof, of the invention can be evaluated for efficacy or potency in a particular preparation or application by, after application to the plant, measuring a net increase in "delayed" root respiration in the plant over the measured time period (at least a three to four hour delay). Thus, measurement of "delayed" root respiration is one means to evaluate the methods and compositions of the invention.

In brief, several strains of bacteria (e.g., Rhizobium meliloti), dead and alive, and natural product isolates purified from R. meliloti, were tested for their ability to increase delayed root respiration of alfalfa (Medicago sativa L.) roots. Maximum respiratory increases, measured either as carbon dioxide gas ($CO_2$) evolution or as oxygen gas ($O_2$) uptake, were elicited in roots of 3-day-old seedlings by 16 hour of exposure to living or dead R. meliloti bacterial cells at densities of $10^7$ bacteria/mL. Excising roots after exposure to bacteria or extracts and separating them into root-tip- and root-hair-containing segments showed that respiratory increases occurred only in the root-hair region. In these assays, $CO_2$ production (generated by "delayed" increases in root respiration) by root hair plant segments increased by as much as 100% in the presence of bacteria, dead or alive.

Whole Bacteria Used as a Test Compound to Enhance Net Photosynthesis

In one embodiment of the invention, whole microorganisms, dead or alive, are applied to plants to enhancer net photosynthesis and subsequent "delayed" net root respiration.

Rhizobium meliloti 1021 (Rm1021) (Meade (1982) J. Bacteriol. 149:114–122) were grown to the early stationary phase in a defined minimal medium (as described in Vincent (1970) In "A Manual for the Practical Study of Root-Nodule Bacteria, Blackwell Scientific Publications, Oxford, UK). Bacteria were collected by centrifugation and washed three times with sterile water before roots were inoculated. UV irradiance for killing cells in some experiments was supplied as a 25 minute treatment with a transilluminator(model T1202, Sigma). The absence of living cells in UV-killed cultures and sterile, non-inoculated control treatments was verified by plating on tryptone yeast medium.

Plant Growth

If respiration is to be measured, it is important that the plants be grown under sterile conditions for the respiration measurements (see, e.g., Guri, et al., U.S. Pat. No. 5,503,652, describing compositions and methods to prevent microbial contamination of plant tissue culture media). Seeds of alfalfa (Medicago sativa L. cv Moapa 69) were surface sterilized for 15 minutes in 70% ethanol, rinsed with water, and allowed to imbibe for four hours with aeration before germinating in a hydroponic system (as in Maxwell (1989) Plant Physiol. 91:842–847) containing nitrogen free nutrient solution (see DeJong (1981) Plant Physiol. 68:309–313). Each 400 mL plastic box contained one gram of seeds and produced about 400 seedlings after being maintained in a sterile manner for about three days with aeration at 25° C. under indirect sunlight supplemented with fluorescent lights. Plants used in these experiments consisted of cotyledons and roots with an occasional primary leaf.

Application of Whole Bacteria to Plants

Experiments used $5 \times 10^7$ colony-forming units (CFU) of bacteria per mL of plant nutrient solution unless otherwise noted. Bacteria were harvested from their growth medium, washed twice in sterile water, suspended in 1 mL of water and added to the plant nutrient solution of alfalfa seedlings 3 days after germination, when roots were approximately 4-cm long. Sterile water (1 mL) was added to the sterile non-inoculated controls. Plants were harvested to measure root respiration at various times, depending of the experiment. At harvest, roots were excised, blotted briefly on a paper towel, weighed, and enclosed in a 10-mL gas-tight test tube. Each replicate contained 1 gram fresh wt of roots from about 200 plants; every experiment had three or four replicates; and all experiments were repeated at least twice.

Respiration Assays

All assays were conducted for 30 minutes immediately after excision. Changes in $CO_2$, and in some experiments $O_2$, were measured at 45° C. with a thermistor detector on a Sigma 4 gas chromatograph equipped with a column (3.05 m×3.2 mm) containing Chromosorb 102 for $CO_2$ and Molecular Sieve 5A for $O_2$. Helium was used as the carrier gas at flow rates of 15 $cm^3$/min for $O_2$ and 35 $cm^3$/min for $CO_2$. The change in gas composition during the first 30 min after the roots were enclosed in the assay tubes (described above) was used to calculate respiration rates. Data were analyzed with standard statistical methods to determine SE or LSD0.05 values for comparisons of treatment effects by Student's t test or analysis of variance (see, e.g., Steel et al., (1960) Principles and Procedures of Statistics. McGraw-Hill, NY).

Results: Bacterial Enhancement of Photosynthesis as Determined by "Delayed" Increases in Root Respiration Experiments in which Rm1021 bacteria were applied to roots of three day old alfalfa seedlings established that soon after four hours, root respiration began to increase significantly ($P<0.05$) relative to sterile, non-inoculated controls. At eight hours after application, the $CO_2$ production went from about 1.5 millimolar per gram (mmol/g) fresh weight per hour (wt/h) to about 2.2 mmol/g fresh wt/h, peaking at about 16 hours at 2.5 mmol/g fresh wt/h. In various experiments, the promotive effect reached a maximum about 8 to 12 hours after inoculation, and remained at high levels for at least 24 hours. $CO_2$ production by the roots was linear for more than one hour after excision. In experiments in which both $CO_2$ production and $O_2$ uptake were measured, the $CO_2$ production increased in proportion to $O_2$ uptake. Germinating seedlings in the presence of 8 mM $NH_4NO_3$ had no effect on these results. All experiments were done under N-free nutrient conditions.

Living bacteria were not required for the respiratory response because UV-killed cells also increased $CO_2$ production by the roots. In fact, dead bacteria elicited significantly higher rates of root respiration than living cells in several, but not all, experiments. For example, R. meliloti Rm1021 enhanced "delayed" root respiration. Roots of three day old seedlings were exposed to living or dead bacterial cells for about 20 hours. Four centimeters (cm) primary roots, including tips, were excised and analyzed, as described above. For both the dead and live Rm1021 cells after application of bacteria (for 20 hours), $CO_2$ production was about 1.0 mmol/g fresh wt/h, as compared to a sterile control at about 0.5 mmol/g fresh wt/h.

Further experiments clearly indicated that the delayed respiratory enhancement by Rm1021 occurred in the root-hair region. Bacteria were exposed to the intact plant and then roots were excised and divided into two sections, a one cm tip and a 3 cm subtending segment, which had differentiated root hairs by day three. Although root tips had a much higher rate of $CO_2$ production, Rm1021 enhanced "delayed" respiration only in the root-hair zone.

Treatments in which different numbers of Rm1021 cells were inoculated onto roots showed that at least $10^7$ colony forming units per mL (CFU/mL) were required for the maximum response. When roots of three-day-old seedlings were exposed to living or dead cells for 16 hours, root hair respiration stimulated by $10^7$ CFU/mL was at about 2.0 to 2.25 mmol/g fresh wt/h., as compared to about 1.5 mmol/g fresh wt/h. stimulated by $10^3$ to about $10^4$ CFU/mL., and about 2.0 1.5 mmol/g fresh wt/h. stimulated by $10^8$ CFU/mL.

The well-characterized LCOs from *Rhizobium meliloti*, which function as NOD factors (see, e.g., Spaink (1995) *Annu. Rev. Phytopathol.* 33:345–368; Savoure (1997) *Plant J.* 11:277–287), were not required for the respiratory response studied in these experiments. Mutant *Rhizobium meliloti* strain TJ1A3, which produces neither Nod-factor LCOs nor root nodules, were fully capable of eliciting increased respiration in alfalfa root segments bearing root hairs after 16 hours of exposure to intact seedlings.

Isolation of Bacterial Natural Products Enhancing NET Photosynthesis (Photosynthate Production and "Delayed" Root Respiration Based on this significant increase in delayed root respiration stimulated by living or dead bacterial cells, R. meliloti bacterial extracts were prepared to identify and purify some of the active (photosynthesis/photosynthate-enhancing) bacterial natural products identified using the methods of the invention.

Purification of photosynthesis/"Delayed" Root Respiration Enhancers

Crude "compound D" was isolated using the following procedure. Supernatant (culture medium) samples from dense *Rhizobium meliloti* 1021 bacterial cultures were collected by centrifugation and treated 4 hours with hydrophobic resin (SM-2 Bio-Beads, 30 g/L, or XAD-4, 10 g/L). Compounds adsorbing to the hydrophobic surfaces were eluted with methanol and dried under vacuum.

High pressure liquid chromatography (HPLC) analysis was next performed on the lipophilic (i.e., Bio-Bead binding) fraction isolated from these culture supernatants. Samples for HPLC were dissolved in water and injected into a HPLC system fitted with an analytical column containing reverse phase C18 resin. the column was then eluted with water at 0.5 mL/min from 0 to 10 min. From 10 to 70 minutes, a linear gradient increasing to 100% methanol was applied. The analysis continued isocratically in 100% methanol for another 20 min. Eluting compounds were monitored with a photodiode array detector. Samples collected every minute were dried by lyophilization. Under these conditions, when the bacterial cells were harvested in early stationary phase, "peak D" (crude preparation of "compound D," see below further characterization) eluted after approximately 75 minutes (no "compound Y" was evident, see discussion, below).

One liter of Rm1021 cell culture filtrate yielded approximately five mg of HPLC "peak D" (purified to "compound D" as described below).

Results: Purified Bacterial Natural Products Found to Enhance NET Photosynthesis as Determined by Increases in "Delayed" Root Respiration Delayed respiration enhancement experiments showed that the partially purified compound from *R. meliloti* 1021, "peak D," increased root respiration at very low, possibly picomolar, concentrations. Peak D was found to increase root respiration slowly, for 8 hours; this enhanced rate was maintained at the higher level. Specifically, very small amounts of the peak D material increased root respiration after intact seedlings had been treated for about 16 hours. Peak D material promoted respiration significantly ($P>0.05$) at $6.7\times10^{-10}$ gram per liter (g/L), where $CO_2$ production was about 1.0 mmol/g fresh wt/h. A 10-fold higher concentration produced a one-half-maximum response. The respiration enhancing effect was maximal at about $10^{-7}$ to $10^{-6}$ g/L. In these experiments, HPLC fractions were supplied to roots of three day old seedlings at the indicated concentrations; respiration was measured 16 hours later; values are means from two replicates, each containing roots of about 200 plants.

Peak D material, tested at about $10^{-6}$ g/L, required about 8 hours to elicit a maximum response, which was maintained until the end of this 20 hour experiment.

The Peak D compound differs from lipo-chitin oligosaccharides active in root nodulation because (a) it does not curl alfalfa root hairs, (b) it is synthesized by bacteria in the absence of known plant inducer molecules, and (c) it is produced by a mutant *R. meliloti* that does not synthesize known lipo-chitin oligosaccharides.

Of note is the finding that some of the partially purified bacterial preparations (identified as HPLC fractions, as discussed above) resembled known pathogenic elicitors because they produced a rapid (e.g., 15-min), transitory increase in respiration. As expected, other partially purified bacterial preparations had no activity.

Example 2

Identifying Enhancers of Net Photosynthesis by Application of Purified Bacterial Extracts The following example details the identification of novel enhancers of net photosynthesis using the alfalfa plant model by further purification of photosynthesis-enhancing extracts from *R. meliloti* 1021, as discussed above. Alfalfa roots were treated with various purified bacterial fractions, described below, and tested for their effect on net photosynthesis by measuring radioactive $^{14}CO_2$ incorporation and translocation of photosynthate to the root of the plant (which, as described above, drives an increase in "delayed" respiration).

Highly purified bacterial natural products, including the "compound D," discussed above, and a second "compound Y," were isolated with the following procedures: Bacterial cells were grown in 7 to 14 L lots of the standard bacterial medium for 8 to 12 days (very late stationary phase). Cells were removed by centrifugation. Hydrophobic material from the supernatant was collected on XAD-4 resin, eluted with methanol, and dried by lyophilization. The resulting pellet was solubilized in water and injected into a preparative HPLC column containing C18 resin, which had been equilibrated in water. The column was eluted at 8 mL/min using the following conditions: 0–12 minutes, water; 12–15 minutes, 30% methanol: 70% water; 15–65 minutes, 35% methanol: 65% water; and 65–112 minutes, 50% methanol: 50% water. Under these conditions, "compound Y" eluted from 55 to 62 minutes and "compound D" eluted from 106 to 112 minutes. The samples were dried by lyophilization.

Compounds D and Y were then individually purified through the following four HPLC conditions:

(a) Purification Compound D

Column 2: A semi-preparative HPLC column containing C18 resin was equilibrated in water, and the compound D sample, solubilized in water, was injected. The column was eluted at 2 mL/minute using the following conditions: 0–4 minutes, water; 4–64 minutes, 35% methanol: 65% water; 64–85 minutes, 40% methanol: 60% water. Under these conditions, compound D eluted from 70 to 76 minutes. The sample containing compound D was dried by lyophilization.

Column 3: A semi-preparative HPLC column containing C18 resin was equilibrated in water, and the compound D sample, solubilized in water, was injected. The column was eluted at 2 mL/minute using the following conditions: 0–6 minutes, water; 6–40 minutes, 20% acetonitrile: 80% water. Under these conditions, compound D eluted from 37 to 39 minutes. The sample containing compound D was dried by lyophilization.

Column 4: An analytical HPLC column containing a mixed-mode resin (C8/cation) was equilibrated in phosphate buffer (0.2M $K_2HPO_4$, pH 4.5), and the compound D sample, solubilized in water, was injected. The column was eluted at 0.5 mL/minute using the following conditions: 0–5 minutes, 100% phosphate buffer; 5–40 minutes, a gradient going from 0 to 35% acetonitrile with the remainder comprised of phosphate buffer; 40–50 minutes, 35% acetonitrile: 65% phosphate buffer. Under these conditions, compound D eluted from 42 to 46 minutes. The sample containing compound D was dried by lyophilization.

Column 5: To remove salt from compound D, an analytical HPLC column containing C18 resin was equilibrated in water, and the compound D sample, solubilized in water, was injected. The column was eluted at 0.5 mL/minute using the following conditions: 0–45 minutes, water; 45–55 minutes 20% acetonitrile: 80% water; 55–75 minutes, a gradient going from 20 to 40% acetonitrile with the remainder comprised of water; 75–90 minutes, a gradient going from 40 to 100% acetonitrile with the remainder comprised of water. Under these conditions, compound D eluted from 83 to 85 minutes. The sample containing compound D was dried by lyophilization. This final product is hereinafter referred to as "purified compound D."

(b) Purification Compound Y

Column 2: A semi-preparative HPLC column containing C18 resin was equilibrated in water, and the compound Y sample, solubilized in water, was injected. The column was eluted at 2 mL/minute using the following conditions: 0–8 minutes, water; 8–20 minutes, 20% methanol: 80% water; 20–50 minutes, 30% methanol: 70% water. Under these conditions, compound Y eluted from 41 to 49 minutes. The sample containing compound Y was dried by lyophilization.

Column 3: A semi-preparative HPLC column containing C18 resin was equilibrated in 5% acetonitrile: 95% water, and the compound Y sample, solubilized in water, was injected. The column was eluted at 2 mL/minute using the following conditions: 0–20 minutes, 5% acetonitrile: 95% water; 20–50 minutes, 8% acetonitrile: 92% water; 50–90 minutes, 10% acetonitrile: 90% water. Under these conditions, compound Y eluted from 80 to 88 minutes. The sample containing compound Y was dried by lyophilization.

Column 4: An analytical HPLC column containing a mixed-mode resin (C8/cation) was equilibrated in phosphate buffer (0.2M $K_2HPO_4$, pH 4.5), and the compound Y sample, solubilized in water, was injected. The column was eluted at 0.5 mL/minute using the following conditions: 0–5 minutes, 100% phosphate buffer; 5–40 minutes, a gradient going from 0 to 35% acetonitrile with the remainder comprised of phosphate buffer. Under these conditions, compound Y eluted from 32 to 35 minutes. The sample containing compound Y was dried by lyophilization.

Column 5: To remove salt from compound Y, an analytical HPLC column containing C18 resin was equilibrated in water, and the compound Y sample, solubilized in water, was injected. The column was eluted at 0.5 mL/minute using the following conditions: 0–45 minutes, water; 45–55 minutes 10% acetonitrile; 55–75 minutes, a gradient going from 10 to 30% acetonitrile with the remainder comprised of water; 75–90 minutes, a gradient going from 30 to 100% acetonitrile with the remainder comprised of water. Under these conditions, compound Y eluted from 82 to 84 minutes. The sample containing compound Y was dried by lyophilization. This final product is hereinafter referred to as "purified compound Y."

Results: Purified Bacterial Natural Products Found to Enhance Net Photosynthesis Purified Compound D Twenty hours after treating alfalfa roots with purified compound D, 25% to 30% increases in net photosynthesis was effected, as measured by radioactive $^{14}CO_2$ incorporation tests. Purified compound D was supplied at approximately 100 pM in solution surrounding roots of three day old alfalfa seedlings. Net photosynthesis was measured as radioactive $^{14}CO_2$ incorporation by exposing randomized treatments of all plants simultaneously for about 15 minutes to $^{14}CO_2$ in a single chamber with thorough mixing of the chamber atmosphere. Data points were means from two to four replicates, each of which contained approximately 400 seedlings.

The isotopic assay for measuring net photosynthesis with $^{14}CO_2$ is described in Sheikholeslam (1980) Botanical Gazette 141:48–52. Briefly, to measure net photosynthesis, intact seedling are placed in a clear plastic box with direct exposure to sunlight or artificial lights. Isotopically labeled $^{14}CO_2$ is generated in the plant chamber by injecting an acid solution through a rubber stopper in the wall of the box and into a beaker containing $^{14}C$-bicarbonate. The $^{14}CO_2$ released by that chemical reaction is distributed throughout the box with a fan. After 15 minutes of photosynthesis in the presence of $^{14}CO_2$, plants are frozen in liquid nitrogen and separated into roots, stems and leaves. The amount of $^{14}CO_2$ is measured in the various plant parts with a scintillation counter after chemical digestion of the plant matter.

Net photosynthesis, i.e., radioactive $^{14}CO_2$ incorporation, increased rapidly after application of the compound D solution at estimated concentrations of no more than 100 pM (see below), peaking after about 5 to 10 hours, depending on the experiment, at about 2.5 to 2.75 $^{14}CO_2$ cpm×$10^5$ per gram exposed alfalfa seedling cotyledon (with a negative control background of about 1.5 $^{14}CO_2$ cpm×$10^5$ per gram cotyledon); and leveling off to about 2.0 $^{14}CO_2$ cpm×$10^5$ per gram cotyledon after approximately 20 hours, the last time point of the experiment. These measurements translate into an increase in net photosynthesis as much as 45% to 75% at the 8 hour (after treating roots) time point above untreated controls before declining to the 20 hours value. At about 20 hours, the increase in net photosynthesis was about 25% to 30% over untreated control.

In another experiment, treating alfalfa seedling roots with purified compound D at a presumed concentration of about 100 pM every 48 hours for 10 days increased the final shoot dry mass (as determined by weighing) 10% relative to untreated control plants. The plants treated with compound D showed no increase in root dry weight because the photosynthate (generated by compound D-enhanced net photosynthesis) subsequently transported to the roots was used to increase dark respiration.

Purified Compound Y

Purified compound Y supplied to alfalfa roots at very low (e.g., picomolar) concentrations also increases alfalfa root respiration and, to a lesser extent, net photosynthesis. These experiments were conducted in the same manner as those described for compound D. The effect of Y on increasing root respiration in various experiments ranged from 11 to 31%, while the promotive effect on net photosynthesis was uniformly low, i.e. no more than a 7% enhancement.

Estimating Molar Concentrations of Compounds D and Y

The actual active concentrations of both D and Y in all experiments reported here are unknown because extinction coefficients cannot be calculated until weighable amounts of the purified compounds are isolated. The estimated concentrations mentioned refer to probable maximum concentrations, which were determined in the following manner: When samples of bacterial medium recovered from the hydrophobic resins were run through the initial preparative HPLC column (see above), weighable amounts of crude Y and D were recovered for further purification. Using the weight of these samples in combination with the estimates of unit molecular weight determined by mass spectrometry (see below), maximum molar concentrations were estimated in various experiments. Using these procedures, rough calculations indicate that the effects of Y on plants require somewhat higher concentrations than D, as evaluated using the experimental protocols discussed above.

Structural Analysis of Compounds D and Y

Proton nuclear magnetic resonance ($^1$H-NMR) analyses of both compounds D and Y show signals consistent with two separate and distinct protons at approximately 7.75 to 8.1 PPM (see Williams, D. H. and I. Fleming. 1987. Spectroscopic Methods in Organic Chemistry. McGraw-Hill, Ltd. London). In addition, signals consistent with two aromatic methyl groups are visible at 2.45 to 2.60 PPM in both compounds D and Y. The values of the two proton signals near 8.0 indicate the protons probably are part of a heterocylic structure. Compound D has an additional proton signal at approximately 8.5 ppm, which is consistent with a proton on an aromatic N atom. Proton NMR spectra from both compounds D and Y are consistent with the presence of several aromatic moieties linked together.

UV-visible absorbance data support these conclusions by showing multiple absorbance bands and a strong fluorescence when illuminated with UV light. Compound D has absorbance maxima at 216, 260, 351, and 390 nm in methanol/water. Compound Y has absorbance maxima at 222, 266, 370, and 445 nm in methanol/water. Both compounds D and Y are degraded by light and heat (e.g., 40° C.).

Unit-resolution mass spectrometry analyses show ions consistent with molecular weights of 770 and 752 atomic mass units (amu) for compounds D and Y, respectively. Both compounds are moderately hydrophobic and can be removed from aqueous solution in $C_{18}$ resin. The purified compounds D and Y are soluble in both water and methanol.

Structures of Compounds D and Y Compared to Known Microbial Natural Products to Identify Additional Enhancers of Net Photosynthesis These structural analyses of compounds D and Y identify a class of organic compositions which may be enhancers of net photosynthesis. Thus, these tentative structural characteristics of compounds D and Y were used to identify other compositions which are enhancers of net photosynthesis.

The structural characteristics of compounds D and Y were compared to the structures of known microbial, especially bacterial natural products, to identify compounds with general structural identity that also may be enhancers of net photosynthesis. A number of soil bacteria, including Pseudomonas species, produce a compound known as 2,4-diacetylphloroglucinol ($C_{10}H_{10}O_5$, also called 2,4-diacetyl-1,3,5-benzenetriol) and monoacetylphloroglucinol. In fact, analysis of these compounds, as described above for compounds D and Y, found that diacetylphloroglucinol increases net photosynthesis in plants by as much as 50% when it is applied to roots in nanomolar concentrations.

Synthesis of 2,4-diacetylphloroglucinol has not been reported in Rhizobium or Sinorhizobium bacteria, but such activity would not be surprising because related, Gram-negative Pseudomonas bacteria do make this molecule. Cells grown on dextrose produce much more of both compounds D and Y than those grown on mannitol. Supplementing the culture medium with 2,4-diacetylphloroglucinol, monoacetylphloroglucinol, or phloroglucinol at final concentrations of 50 micromolar increased production of compound D by about 60% to 70%, but this procedure had no consistent effect on the production of compound Y.

What is claimed is:

1. A method for increasing net photosynthesis in a plant, the method comprising applying to a root of the plant a composition comprising an agent selected from the group consisting of triacetylphloroglucinol, diacetylphloroglucinol and monoacetylphloroglucinol in an amount effective for increasing net photosynthesis in the plant.

2. The method of claim 1, wherein said composition thus applied comprises a bacterium capable of generating the agent.

3. The method of claim 2, wherein said bacterium is selected from the group consisting of *Sinorhizobium meliloti*, or *Pseudomonas fluorescens*.

4. The method of claim 2, wherein said bacterium is applied in a concentration of about $10^7$ to about $10^8$ bacteria per mL.

5. The method of claim 1, wherein said composition thus applied comprises a bacteria culture media.

6. The method of claim 1, wherein said composition thus applied comprises an isolated bacterial product.

7. The method of claim 6, wherein said bacterial product is isolated by chromatography.

8. The method of claim 1, wherein said composition thus applied comprises a diacetylphloroglucinol.

9. The method of claim 8, wherein said diacetylphloroglucinol is 2,4,-diacetylphloroglucinol.

10. The method of claim 1, wherein said agent is in a concentration of about 50 to about 100 nM and the composition is applied to the root of said plant.

11. The method of claim 1, comprising applying said composition to said plant in multiple applications.

12. The method of claim 1, comprising applying said composition to said plant about every 24 to 48 hours.

13. The method of claim 1, wherein said plant is an angiosperm.

14. The method of claim 13, wherein said angiosperm selected from the group consisting of monocotyledonous plants and dicotyledonous plants.

15. The method of claim 14, wherein said dicotyledonous plant is a legume.

16. The method of claim 15, wherein said legume is alfalfa.

17. A method for increasing net photosynthesis in a plant, the method comprising applying to said plant a composition comprising a bacterium, wherein the composition is applied in an amount effective to increase net photosynthesis in the plant, wherein the bacterium is selected from the group consisting of *Sinorhizobium meliloti* and *Pseudomonas fluorescens*.

18. The method of claim 17, wherein the bacterium is *Sinorhizobium meliloti*.

19. The method of claim 18, wherein the bacterium is *Pseudomonas fluorescens*.

20. The method of claim 1, wherein the plant is of a genus selected from the group consisting of Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Oryza, Panieum, Pannesetum, Persea, Phaseolus, Pisum, Pyrus, Prunus, Raphanus, Secale, Senecio, Sinapis, Solanum, Sorghum, Trigonella, Triticum, Vitis, Vigna, and, Zea.

21. A method for increasing net photosynthesis in a plant, the method comprising applying to said plant a composition comprising an agent selected from the group consisting of triacetylphloroglucinol, diacetylphloroglucinol and monoacetylphloroglucinol to the plant in an amount effective for increasing net photosynthesis in the plant, with the proviso that the plant is not from the genus Nicotiana.

* * * * *